United States Patent
Warsi et al.

(10) Patent No.: US 11,725,509 B2
(45) Date of Patent: Aug. 15, 2023

(54) ROBUST CARBON DOTS (CD) AS AN ARTIFICIAL TRACER FOR GROUNDWATER STUDIES

(71) Applicant: COUNCIL OF SCIENTIFIC & INDUSTRIAL RESEARCH, New Delhi (IN)

(72) Inventors: Taufique Warsi, Hyderabad (IN); Lopamudra Bhattacharjee, Coimbatore (IN); Thangamani Suppan, Coimbatore (IN); Sanjeev K. Jat, Coimbatore (IN); Kallol Mohanta, Coimbatore (IN); Rama Ranjan Bhattacharjee, Kolkata (IN); Rangarajan Ramaswamy, Hyderabad (IN); Chakravadhanula Manikyamba, Hyderabad (IN); T. Vinoda Rao, Visakhapatnam (IN); Virendra Mani Tiwari, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 223 days.

(21) Appl. No.: 17/146,346

(22) Filed: Jan. 11, 2021

(65) Prior Publication Data
US 2022/0220848 A1      Jul. 14, 2022

(51) Int. Cl.
*E21B 49/08*   (2006.01)
*G01N 33/18*   (2006.01)
*G01N 21/77*   (2006.01)

(52) U.S. Cl.
CPC ......... *E21B 49/0875* (2020.05); *G01N 21/77* (2013.01); *G01N 33/18* (2013.01); *G01N 2021/7786* (2013.01)

(58) Field of Classification Search
CPC .......... E21B 47/11; E21B 43/26; E21B 43/16; E21B 49/086; E21B 49/088
See application file for complete search history.

(56) References Cited

U.S. PATENT DOCUMENTS

2012/0318503 A1    12/2012  Kanj et al.
2016/0363693 A1*   12/2016  Murugesan .......... G01N 21/643

FOREIGN PATENT DOCUMENTS

WO    WO-2012116189 A2 *  8/2012    ......... B23K 26/0093

OTHER PUBLICATIONS

Davis, SN., Thompson, GM., Bentely, GE. and Stiles, S. 1980. Ground-Water Tracers—A Short Review. Groundwater 18 (1), 14-23. https://doi.org/10.1111/j.1745-6584.1980.tb03366.x.

(Continued)

*Primary Examiner* — Zakiya W Bates
(74) *Attorney, Agent, or Firm* — Maschoff Brennan (57) ABSTRACT

The disclosure provides methods for the measurement of ground water characteristics. The carbon dot tracer is injected in an injection bore well. Carbon dot tracer and ground water are thoroughly mixed in the injection bore well. The ground water mixed with carbon dot tracer is pumped from the injection bore well to an acquiring bore well connected with injection bore well with micro and major fracture; the water samples mixed with carbon dot tracer were collected at the acquiring bore well. The characteristics of the ground water were measured by measuring fluorescence. The disclosure further relates to a method for depicting the solute transportation in the soil.

11 Claims, 10 Drawing Sheets

(56) References Cited

OTHER PUBLICATIONS

Leibundgut, C. 1995. Tracer technologies for hydrological systems. International Association of Hydrological Sciences.

Maurice, L., Barker, JA., Atkinson, TC., Williams, AT. and Smart, PL. 2011. A Tracer Methodology for Identifying Ambient Flows in Boreholes. Groundwater 49 (2), 227-238. https://doi.org/10.1111/j.1745-6584.2010.00708.x.

Sankaran, s., Rangarajan, R. and Dhar, RL. 2005. Delineation of hydraulic connectivity across a dolerite dyke through hydrogeological, geophysical and tracer studies—A case study. Environmental Geology 48(4):411-419.

Puri, S., Kumar, P., Rana, S., Kr, B., Debnath, S., Ghanshyam, C. and Kapur, P. 2014. GIS-Based Geospatial Mapping of Arsenic Polluted Underground Water in Purbasthali Block in Bardhaman, West Bengal. International Conference on Communication and Computing (ICC—2014), At Bangalore.

Ramakrishnaiah, CR. and Manasa, N. 2016. Distribution and Migration of Heavy Metals in Peenya Industrial Area, Bangalore, Karnataka, India—A Case Study. Journal of Geography, Environment and Earth Science International 6, 1-13. DOI:10.9734/JGEESI/2016/26361.

Drost, W., Klotz, D., Koch, A., Moser, H., Neumaier, F. and Rauert, W. 1968. Point dilution methods investigating ground water flow by means radioisotopes. Water resources research 4 (1), 125-146.

Leibundgut, Chris. 1995. Tracer technologies for hydrological systems. Proceedings of an international symposium, Colorado.

McCance, W., Jones, OAH., Edwards, M., Surapaneni, A., Chadalavada, S. and Currell, M. 2018. Contaminants of Emerging Concern as novel groundwater tracers for delineating wastewater impacts in urban and peri-urban areas. Water research 146. 118-133.

Winter, F. 2006. Using tracer techniques to investigate groundwater recharge in the Mount Carmel aquifer Israel, Ph.D Thesis. Albert ludwing university, Freiburg.

Sanford, WE., Hertig, WA. and Herczeg, L. 2011. Preface: Insights from environmental tracers in groundwater systems. Hydrogeology Journal 19, 1-3.

Subramanian, SK., Li, Y. and Cathies, LM. 2013. Assessing preferential flow by simultaneously injecting nanoparticles and chemical tracers. Water resources research 49, 29-42.

Yuce, G. and Gasparon, M. 2013. Preliminary risk assessment of radon in groundwater: a case study from Eskisehir, Turkey. Isotopes in environmental and health studies 49 (2), 163-179.

Salim, HS. 2011. Applications of nanoparticle image velocimetry in nanofluids, Master's Thesis, University of Tennessee.

Tchemiak, A., Prakash, A., Mayo, JT., Colvin, VL. and Link, S. 2009. Fluorescence correlation spectroscopy of magnetite nanocrystal diffusion. J. Phys. Chem. C. 113, 844-848.

Berkowitz, B. 2002. Characterizing flow and transport in fractured geological media:A review. Advances in Water Resources 25, 861-884.

Fundamental mechanisms. Hydrogeology Journal 11 (4), 418-433, undated.

James, C.A., Miller-Schulze, J.P., Ultican, S., Gipe, A.D. and Baker, J.E. 2016. Evaluating Contaminants of Emerging Concern as tracers of wastewater from septic systems. Water Research doi: 10.1016/j.watres.2016.05.046.

Cohen, M. and Weisbrod, N. 2017. Transport of iron nanoparticles through natural discrete fractures, Water Research. doi:10.1016/j.watres.2017.11.019.

Hung, YL., Hsiung, TM., Chen, YY., Huang, YF. and Huang, CC. 2010. Colorimetric detection of heavy metal ions using label-free gold nanoparticles and alkanethiols. J. Phys. Chem. C. 114, 16329-16334.

Kanel, SR., Goswami, RR., Clement, TP., Barnett, MO. and Zhao, D. 2008. Characteristics of surface stabilized zero-valent iron nanoparticles in porous media. Environ. Sci. Technol. 42, 896-900.

Sharma, P., Brown, S., Walter, G., Santra, S. and Moudgil, B. 2006. Nanoparticles for bioimaging. Advances in colloid and interface science 123, 471-485.

Divine, C. and Mcdonnell, J. 2005. The future of applied tracers in hydrogeology. Hydrogeology Journal 13. 255-258. DOI:10.1007/s10040-004-0416-3.

Geuther, J., Podowski, M., Danon, Y. and Block, R. 2019. Development of a Nanotracer Method to Characterize Nanoparticle Coatings. Isotopes and Radiation: General, 784.

Bhattacharjee, L., Manoharan R., Mohanta, K. and Bhattacharjee, RR. 2015. Conducting carbon quantum dots—a nascent nanomaterial. J. Mater. Chem. A 3, 1580-1586. DOI: 10.1039/C4TA05491A.

Bhattacharjee, L., Mohanta, K., Pal, K., Koner, AL. and Bhattacharjee, RR. 2016. Polarization induced dynamic photoluminescence in carbon quantum dot-based ionic fluid J. Mater. Chem. A 4, 2246-2251.

Bhattacharjee, L., Pal, Jat, SK., Koner, AL., Ravichandran, J. and Bhattacharjee, RR. 2017. Tuning optical properties of printable carbon quantum dots using near-field environment. Carbon 125, 409-418. https://doi.org/10.1016/j.carbon.2017.09.030.

\* cited by examiner

ROBUST CARBON DOTS (CD) AS AN ARTIFICIAL TRACER FOR GROUNDWATER STUDIES

FIELD OF INVENTION

The present invention relates to carbon-based nano-agents as an artificial tracer for ground water studies. In particular, the present invention relates to method for the measurement of ground water characteristics using carbon dots (cd) as artificial tracer and carbon dots (cd) used thereof.

BACKGROUND OF INVENTION

Artificial tracers are defined as substances which are added intentionally to hydrological systems in planned experiments. The scales of application of artificial tracers are limited in both time and space. In general, artificial tracers are used in systems, which have a residence time of less than 1 year. On the other hand, artificial tracers allow labeling specific parts of a hydrological system.

The demand for creative ways to predict availability and sustainability of underground and surface water resources is necessary. Isotope and tracer techniques provide critical parameter on source, age, interconnectivity, flow rate and direction of groundwater along with its migration rate (Davis 1980, Leibundgut 1995, Sankaran 2005 and Maurice 2011). The same techniques can also provide information on the pathways of contaminants present in ground water on a local and regional scale levels for better water quality management and remedial measures (Puri 2014 and Ramakrishnaiah 2016). The arrival concentration and arrival time of tracers can be used in determining ground water movement as well as diffusion of contaminants (Drost 1968, Leibundgut 1995, Winter 2006 and McCance 2018). Tracer technology is the only technology which can provide the information regarding the contaminant "plume dimension", direction and its vector (Leibundgut 1995 and Puri 2014).

The most commonly used chemical tracers that are added to ground water are radioactive substances, salts and fluorescent dyes. There are certain factors that may limit the use of conventional radioactive elements and molecular tracers (Sanford 2011 and Yuce 2013). The use of radioactive elements as tracers has potential hazardous effects on the environment especially on human beings and other animals, for which it is currently replaced by non-radioactive elements.

The issue with non-radioactive molecular tracers is their dimension. The diffusion coefficient values of these tracers are very high for their molecular dimensions as per Newton's law of diffusion (Tcherniak 2009, Salim 2011 and Subramanian 2013). Hence, when these tracers are injected in to bore-wells, they diffuse into the rock strata and require long time to eventually come out of the bore-wells and some of the tracers are highly interactive and alter in the subsurface which cannot be considered as a tracer (Berkowitz 2002, Bodin 2003, James 2016 and Cohen 2017). Thus, analysis of ground water flow and contaminant detection becomes time consuming and more expensive. Molecular contaminants are also used as tracers, but due to their size, they penetrate and diffuse very fast. Thus, retrieving tracer samples and their analysis becomes troublesome.

Colloidal water-dispersible nanoparticles have unique physical and chemical properties. They are heavily used in applications such as drug delivery and bio labeling (Sharma 2006, Hung 2010 and Kanj 2012). The properties that complement such applications include easy detection, controlled diffusion, chemical inertness, and non-toxic nature. Colloidal dimensions of nanoparticles provide lower values of diffusion coefficient than molecular tracers and hence their extent of diffusion is far less than the molecular tracers (Kanj 2012).

The nanoparticles may not diffuse from the channels of fluid flow into the adjacent rock as do chemical tracers. The nano-tracers can therefore reveal how a seep fluid leaving one part of a well short-circuits to a recovery well after only perhaps a week rather than months of injection (Kanel 2008 and kanj 2012). Furthermore, comparing the arrival of chemical and nanoparticle tracers, one can show the extent of channeled flow which can be important for certain contaminant remediation. Since nanoparticles can be tagged with bar codes of different fluorescent color, a many tracer experiments could be run simultaneously in a reservoir, providing a great deal of information about fluid movements (Divine 2005). The data can be useful to track contaminant plume movement though reports on such studies with colloidal nanoparticles are rare (Geuther 2019).

Therefore, there is a need for the artificial tracer which possess interesting optical and electronic properties for the measurement of ground water characteristics. Also, there is a need for an environmentally safe and economic method for the measurement of ground water characteristics.

OBJECTIVES OF THE INVENTION

An objective of the present invention is to provide a method for the measurement of ground water characteristics that overcomes many of the disadvantages of the prior art.

Another object of the present invention is to provide a non-radioactive, environmentally friendly and economic method for the measurement of ground water characteristics.

Still another objective of the present invention is to use easily accessible, cheap, non-radioactive, environmentally friendly, highly fluorescent Robust carbon dots (cd) as an artificial tracer for groundwater studies.

Also, the geophysical nano-tracers can be detected in ground water without interference of any other fluorescent compound or material that may or may not be present in ground water.

SUMMARY OF INVENTION

In an embodiment, the present invention relates to a method for the measurement of ground water characteristics, the method comprising:
a. injecting a carbon dot tracer in an injection bore well;
b. mixing the carbon dot tracer and ground water in the injection bore well of step a);
c. pumping the ground water mixed with carbon dot tracer of step b) from the injection bore well to an acquiring bore well connected with injection bore well with micro and major fracture;
d. collecting the water samples mixed with carbon dot tracer at the acquiring bore well;
e. measuring fluorescence of the collected water sample mixed with carbon dot obtained in step d) to obtain the characteristics of the ground water.

In another embodiment, the injection bore well and the acquiring bore well are made of hard rock of terrane selected from Granitoid rock or basalt.

In yet another embodiment, the injection bore well and acquiring bore well are at a depth of 48 m and 49 m respectively.

In another embodiment, the pumping of ground water mixed with carbon dot tracer is done through a submersible pump of 1-5 HP with the in-situ pH range of 6-8.

In the preferred embodiment, the carbon dot tracer is polystyrene sulphonate-coated carbon dots of particle size of 7-8 nm.

In an embodiment, the concentration of carbon dot tracer is 100 ppm in the borewell.

In a preferred embodiment, method for the measurement of ground water characteristics comprising:
a. injecting a polystyrene sulphonate-coated carbon dot tracer in an injection bore well;
b. mixing the tracer and water of step (a);
c. pumping the ground water mixed with tracer of step (b) from the injection bore well to an acquiring bore well by a submersible pump;
d. collecting the water samples mixed with tracer at the acquiring bore well of step (c);
e. measuring fluorescence of the collected water samples mixed with tracer of step (d) to obtain the characteristics of the ground water,
wherein the acquiring bore well is connected to the injection bore well with micro and major fracture.

In another aspect, the present invention relates to a method for depicting the solute transportation in the soil, the method comprising
i) fabricating columns packed with soil sample;
ii) introducing a carbon dot tracer at the top of the fabricating column of step i);
iii) adding deionized water from the top of the column after 3 h of tracer introduction;
iv) collecting leachates with tracers obtained from bottom of the column after addition of deionized water at regular intervals;
v) measuring the fluorescence of tracers in the leachate obtained in step iv) to depict the solute transportation in the soil sample.
vi) In fabricated column, three tracers (viz CD, Chloride and Tritium) were used to understand the comparative movement of CD with conventional tracers.

In an embodiment, the method further comprising saturating soil of the fabricating column of step i) above with deionized water 24 hours before the introduction of tracer.

In a preferred embodiment, the present invention relates to a method for depicting the solute transportation in the soil, the method comprising
i) fabricating column of height 10 cm to 3 m and diameter of less than 100 cm is packed with soil sample;
ii) introducing polystyrene sulphonate-coated carbon dots tracer at the top of the fabricating column of step i);
iii) adding deionized water from the top of the column after 3 h of the tracer introduction;
iv) collecting the leachates with tracer obtained from bottom of the column at regular intervals;
v) measuring fluorescence of the tracers in the leachates obtained in step (iv), to depict the solute transportation in the soil samples.

BRIEF DESCRIPTION OF THE DRAWINGS

So that the manner in which the features, advantages and objects of the invention, as well as others which will become apparent, are attained, and can be understood in more detail, more particular description of the invention briefly summarized above may be had by reference to the embodiments thereof which are illustrated in the accompanying drawings that form a part of this specification. It is to be noted, however, that the drawings illustrate only several embodiments of the invention and are therefore not to be considered limiting of its scope as the invention may admit to other equally effective embodiments. The present technology will be better understood on reading the following detailed description of non-limiting embodiments thereof, and on examining the accompanying drawings, in which.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein and provided in the appended figures are set forth without any loss of generality, and without imposing limitations, relating to the claimed invention.

In an aspect, the present invention relates to a method for the measurement of ground water characteristics, the method comprising:
 a. injecting a carbon dot tracer in an injection bore well;
 b. mixing the carbon dot tracer and ground water thoroughly in the injection bore well of step a);
 c. pumping the ground water mixed with carbon dot tracer of step b) from the injection bore well to an acquiring bore well connected with injection bore well with micro and major fracture;
 d. collecting the water samples mixed with carbon dot tracer at the acquiring bore well;
 e. measuring fluorescence of the collected water sample mixed with carbon dot obtained in step d) to obtain the characteristics of the ground water.

In an embodiment of the present invention, the carbon-based nanomaterials i.e., carbon nano dot tracers are environment friendly, cheap, and easily scalable. They can be easily handled and stored in large quantities, require very less amounts compared to conventional tracers. Further they do not need any agency approval for field usage. Also, the carbon dots used are chemically & physically inert to be used as water tracers for studying ground water activity which comprises of 7-8 nm carbonaceous nano dots that possess very high quantum efficiency and hence detectability in natural ground water samples and which also poses non-sticking properties and are environmentally friendly, easily available, easy to use and finally can be easily synthesized in industrial scales.

Also, the presently used carbon dots shows better diffusion control as compared to the existing tracer materials.

In yet another embodiment of the present invention shows that on modification with suitable ion-exchange functional groups, the carbon nanomaterial can act as nano-resin that can work as nano-resin for enhanced recovery applications.

In a preferred embodiment, the carbon dot tracer is polystyrene sulphonate-coated carbon dots (CDs) (PSS-CDs).

According to the embodiments disclosed herein, a method of forming carbon dots includes the following synthesis protocol:

Chemicals:

Citric acid (CA) (99.7%) was purchased from Himedia Chemicals. Poly (sodium 4-styrene sulfonate, 99.8%, M.W. 70 000) (PSS) and 8-anilino-1-naphthalenesulfonic acid (1,8-ANS) were purchased from Sigma-Aldrich, and they were used as received without further purification. All acids and bases used were purchased from Loba and used as received. Dialysis membranes were purchased from Himedia. Milli-Q water was used in all the experiments. Jeffamine was obtained from HUNTSMAN (India) as gifted sample and was used without purification.

Synthesis of Carbon Dots (PSS-CDs) in Large-Scale for Laboratory & Field Test 90 g of citric acid is dissolved in water in a beaker. In another beaker 15 g PSS polymer was dissolved in water. Both the solutions were stirred vigorously for few hours and mixed together.

After mixing, solution was kept on stirring for 2 h and kept on water bath for drying at 75° C. Evaporation of water produces a honey like liquid mixture of citric acid and PSS. The mixture was kept in vacuum oven at 60° C. for one day. After drying, the mass was pyrolyzed in muffle furnace at 200° C. for 2 h. Produced mass was taken out of furnace as it comes down to room temperature after pyrolysis. Product was black color powder (PSS-CDs) having approximate weight of 18 g.

In the same way 5 batches of samples were prepared for tracer tests to scale up the amount of CDs. This was required for laboratory and field tests. Gravimetric and thermogravimetric estimations indicate that 53% (w/v) of the PSS-CDs are PSS and the rest (47% w/v) are pure CDs. The fluorescence emission mentioned in the following sections originates from the 47% CD materials. PSS do not contribute to any fluorescence emission but its role is to passivate the surface of the CDs in order to control its nano-domain as well as increase the dispersibility of the CDs in water.

Preparation of CD-Tracer Standards and Calibration

Figure 1:
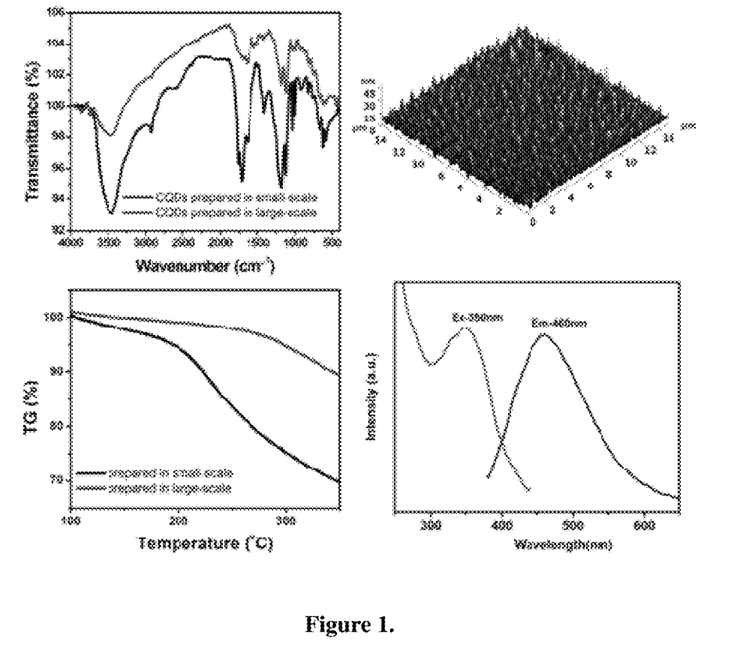
FIG. 1. represents the various characteristics of the CDs. (a) FTIR spectra of PSS-CDs prepared in tubular furnace (small-scale) and in muffle furnace at (large-scale); (b) TGA of PSS-CDs prepared at in tubular furnace (small-scale) and in muffle furnace (large-scale); (c) AFM image of spin-coated PSS-CDs; (d) Fluorescence excitation & emission spectra of the PSS-CDs.
Figure 2:
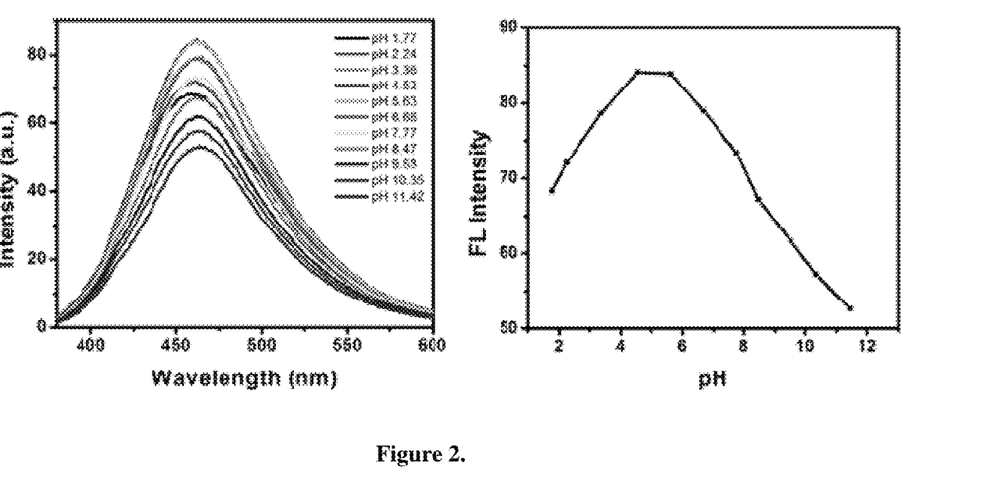
FIG. 2. represents pH dependency of emission spectra of PSS-CDs. Spectra recorded after excitation at 340 nm. The spectra indicate the chemical robustness of the CDs.
Figure 3:
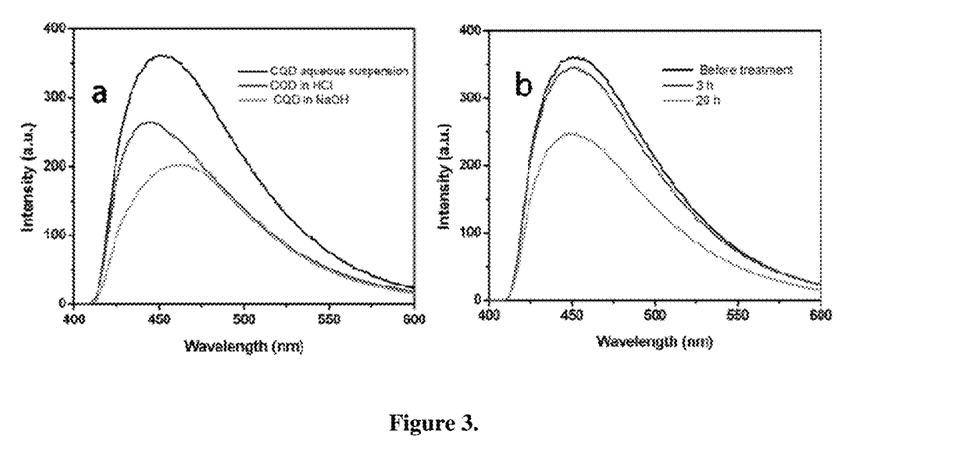
FIG. 3. represents (a) Emission spectra of PSS-CDs dispersed in alkali & acid; (b) Emission spectra of PSS-CDs recorded after temperature & pressure treatment. All spectra were recorded at excitation of 340 nm. The spectra indicate the chemical robustness of the CDs.
Figure 4:
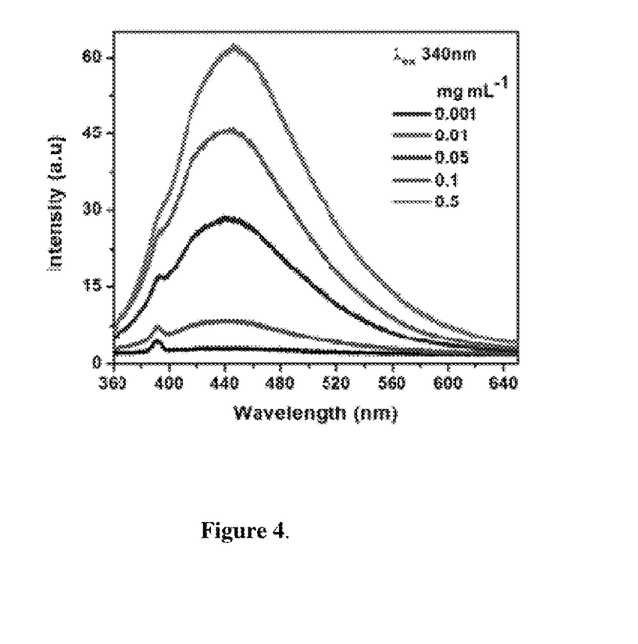
FIG. 4. represents concentration dependent emission spectra of PSS-CDs dispersion in water. All the spectra are obtained at excitation of 340 nm. The spectra indicate the detection limits of the CDs in ground water.
Figure 5:
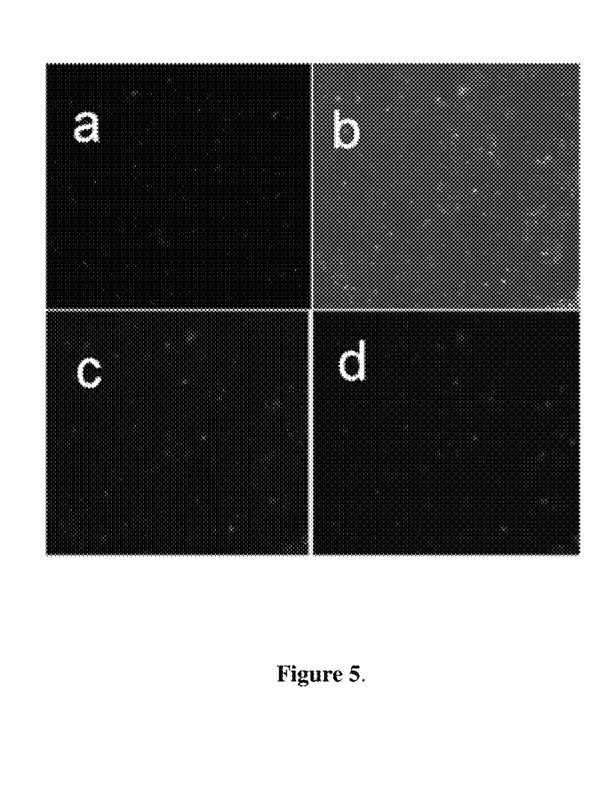
FIG. 5. represents (a) EPI-fluorescence image of drop casted PSS-CDs under UV-filter; (b, c & d) EPI-fluorescence image of spin-coated PSS-CDs under UV, blue and green filter respectively. All images were obtained at 20× magnification. The data indicates how easily the CDs can be detected in ground water samples using a simple fluorescence microscope.
Figure 6:
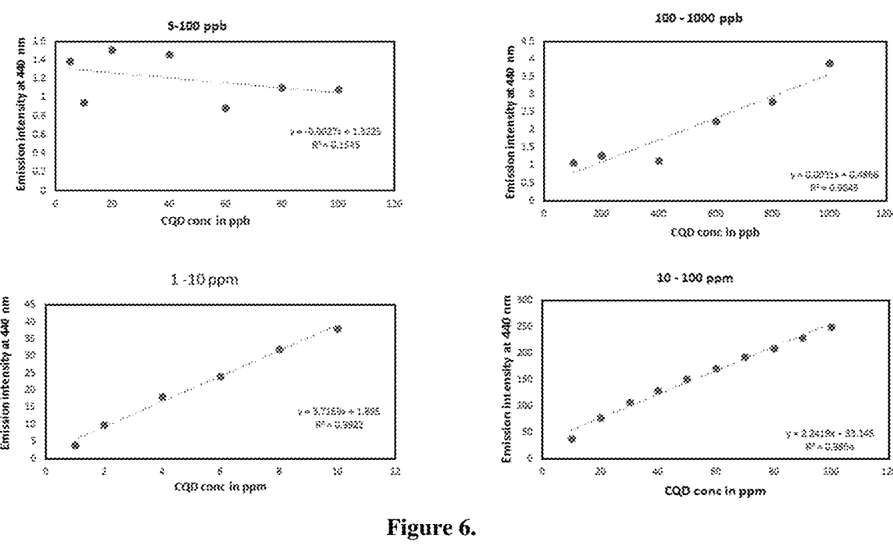
FIG. 6. represents standard calibration curve (Emission intensity 440 nm) wrt standards for laboratory experiment.

The PS S-CD material obtained through synthesis was used for preparation of various standards and for its testing and calibration. 0.2 g of vacuum-packed PSS-CD sample is mixed with 200 ml of double distilled water in 500 ml beaker to make 1000 ppm concentration. The content is stirred in magnetic stirrer for 6 h. Various concentrations from 100 ppm to 5 ppb were prepared from the main standard through progressive dilution (FIG. 6).

Figure 7:
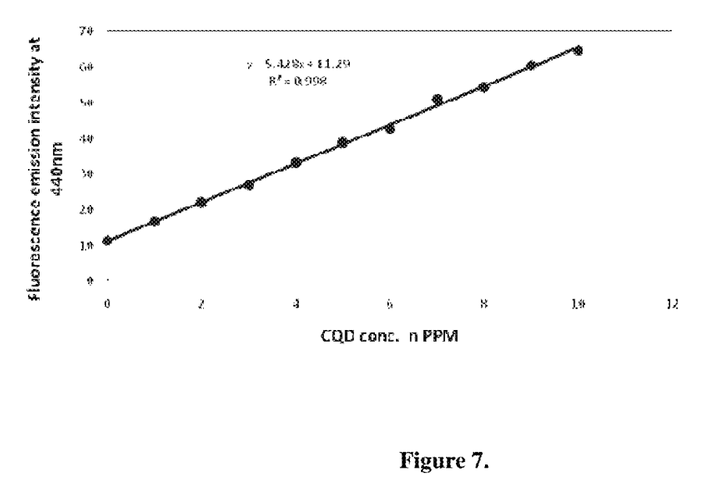
FIG. 7. represents standard calibration curve (Emission intensity 440 nm) wrt standards for field experiments.

Preparation of CD Standards and Calibration Using Aquifer Water 0.2 g of vacuum packed PSS-CD sample is mixed with 200 ml of aquifer water of the experimental site (Maheshwaram watershed, Telangana, India) in 500 ml beaker to make 1000 ppm concentration. The aquifer water is obtained after the bore well is pumped for more than 1 h. The content is stirred in magnetic stirrer for 6 h. Various concentrations from 1 to 10 ppm were prepared from this main standard through progressive dilution using aquifer water (FIGS. 6 & 7).

The samples were analyzed in LS55-Perkin Elmer Fluorescence spectrometer with the instrument setting as; Excitation: 340 nm, Emission range: 360-550 nm, Excitation slit width: 3.5 nm, Emission slit width: 3.5 nm, scan speed: 100 nm/min. The standards were measured with above parameters. The emission intensity data obtained for various standards were correlated. The best fit line drawn, and the regression equations shows linear correlation with the correlation coefficient of 0.99.

Column Preparation for Lab Scale Tracer Studies

Column A was packed with fine sand, column B with coarse sand, column C with coarse textured red soil and column D with medium textured red soil (Table 1). The height and diameter of the PVC columns are 1.86 m and 0.2 m respectively. Closed PVC cap with holes and wire mesh were provided in the bottom of the tube for the infiltrated water to escape from the column. PVC mesh was also provided at the top of the sand column. About 10 cm open space above the top surface of soil/medium is provided for storing input water.

Tracer Tests in Laboratory Columns 0.1 g of PSS-CDs mixed in 100 ml deionized water and was stirred continuously using magnetic stirrer for 2 days. This was used for preparation of 1000 mg/l and 500 mg/l PSS-CD tracer. Tritium activity of 5 millicurie/ml was used for preparation of 25 microcurie/ml tritium tracer. Analar grade sodium chloride powder was used for preparation of 2000 mg/l chloride tracer. The combination of these tracers was used to study their relative movement in the geological medium under simulated conditions. Before the column experiments, standards of various concentrations were prepared for calibrating the equipment fluorescence spectrometer and to know the order of fluorescence emission intensity values for various concentrations (FIG. 6).

Fluorescence Studies

The samples were analyzed in LS55-Perkin Elmer Fluorescence spectrometer which provides emission intensity and thus concentration of PSS-CD. From the various trial experiments carried out, the excitation energy, emission energy range, excitation slit width, emission slit width, scan speed was identified for determining the actual concentration of PSS-CD. The parameters identified are; Excitation: 340 nm, Emission range: 360-550 nm, Excitation slit width: 3.5 nm, Emission slit width: 3.5 nm, scan speed: 100 nm/min. The standards were measured with above parameters. This parameter was used for all the samples collected from laboratory and field testing. The emission intensity data obtained for various standards were correlated with concentrations in 4 different plots (5-100 ppb, 100-1000 ppb, 1-10 ppm and 10-100 ppm) (FIG. 6) The best fit line drawn for all the plots and the regression equations shows linear correlation between emission intensity and PSS-CD concentration (FIG. 6&7). The correlation coefficient is very poor for concentration ranging from 5-100 ppb. However good correlation is observed for concentrations range 100-1000 ppb, 1-10 ppm and 10-100 ppm with correlation coefficient more than 0.9. Thus, the signal can be clearly picked for concentrations greater than or equal to 100 ppb. The regression equation can be used for determining PSS-CD concentration of unknown sample. This experiment also enables to use optimum PSS-CD concentration for laboratory trials and field experiments.

Cell Culture

MDA MB 453 (Human breast cancer cell line) was obtained from NCCS Pune. It was maintained in Roswell Park Memorial Institute (RPMI) supplemented with 10% fetal bovine serum (FBS), 2 mM glutamine, amphotericin (3 µg/ml), gentamycin (400 µg/ml), streptomycin (250 µg/ml), penicillin (250 units/ml) and 1 mg/ml insulin in the incubator at 5% $CO_2$, 37° C.

CD-Polymer Composite

The PSS-CDs are treated with acid-resin to convert the —$SO_3Na$ groups to —$SO_3H$. The pH was recorded to be 2.5. To the acidic CD-PSS, drop-wise Jeffamine solution was added until steady pH reading of 5.5 is obtained.

Serial Dilution Preparation for Testing

The CDs and CDs-polymer were dissolved in DMSO separately to get a stock concentration of 50 µg/µl. The stock solution was then serially diluted in DMSO to get a final concentration of 0.001, 0.01, 0.1, 1, 10, 50 and 100 µg/ml. Finally, it was added to the wells containing culture medium of 200 µl.

MTT Assay

Cell lines were maintained in RPMI supplemented with 10% FBS, 2 mM glutamine, amphotericin (3 µg/ml), gentamycin (400 µg/ml), streptomycin (250 µg/ml) and penicillin (250 units/ml) in a carbon dioxide incubator at 5% $CO_2$. Approximately $2 \times 10^4$ cells/well were seeded in 96 well plate using culture medium, the viability was tested using trypan blue dye with help of haemocytometer and 95% of viability was confirmed. After 24 h, the fresh medium with the extracts were added at respective wells and kept incubation for 48 h. After incubation the following assays were performed.

After 48 h of the drug treatment the fresh medium was changed again for all groups and 10 µl of MTT (5 mg/ml stock solution) was added and the plates were incubated for an additional 4 h. The medium was discarded and the formazan blue, which was formed in the cells, was dissolved with 100 µl of DMSO. The optical density was measured at 570 nm. The percentage toxicity was calculated by using following formula. Graph pad prism software was used to calculated IC50 of the extracts=percentage toxicity=1−treated cells/untreated cells×100.

Measurement Techniques

Tritium was detected in high background Liquid scintillation counter; Chloride was estimated by Titrimetric method with silver nitrate solution and potassium dichromate as indicator. CD fluoropores (CP) was detected by Fluorescence Spectrometer (Perkin Elmer). Data acquisition and instrumental parameters are controlled from FL Winlab software. For CD-tracer, emission maxima of PSS-CD suspension were recorded in FL spectrophotometer. Emission maxima for CDs were recorded at 440 nm while exciting at 340 nm. PSS-CD water suspensions were prepared at different concentrations. In order to examine the CD performance, fluorescence activity was measured for the lab samples as well as for the field samples. The lab samples were collected in the form of leachates released from the bottom of the column at discrete time interval and cumulative for each specific interval of time and similar experimental investigations were carried out for various soil types. The similar characterized PSS-CDs were used in field experiment with the multi well technique followed by sample collection which was carried out in the direction of flow at acceptor well. The water samples collected during lab and field experiment were taken to the Fluorescence spectroscopy lab for measuring fluorescence intensity, after thoroughly cleaning the cuvettes, samples were transferred in the order and loaded to the sample holder socket of the spectrometer. Samples were excited at 340 nm with the slit width of 3.5 nm at 100 nm/min of scan speed.

Bore Hole Tracer (Aquifer Tracer Tests)

Natural groundwater flow is usually found to be laminar, which specifies that the velocity of groundwater flow is proportional to the hydraulic gradient. The relationship known as Darcy's law can be expressed as;

$$Vn = Kj$$

where,
v=pore velocity of groundwater
n=effective porosity of an aquifer
k=hydraulic conductivity of an aquifer
j=hydraulic gradient Single well and multi well methods can be used for estimating groundwater velocity. (Drost 1968). In the single well method, the groundwater column of a filter tube/bore well is labeled with a tracer solution. The decrease in the concentration of this solution in time scale is a function of groundwater flow across the well. It can be expressed as, Groundwater filtration velocity (v*) is given as $$Q = \frac{V}{t} \ln \frac{C_0}{C} \quad (1)$$

$$V^* = \frac{V}{At} \ln \frac{C}{C_0} \quad (2)$$

$$V^* = pnv \quad (3)$$

Where,

Q=groundwater discharge from the filter tube
V=volume of labeled water column
$C_0$=concentration of the labeled water column at time t=0
C=concentration of the labeled water column at time t
A=flow cross section area of the tube
v*=filtration velocity
pn=effective porosity of the aquifer
v=distance velocity of groundwater In the multi well technique, a labeling substance is added to the groundwater at an injection point (donor well). Detection is carried out in the direction of flow at acceptor wells. The measured parameter is time taken by the labeled water when the flow is from the donor well to the acceptor well. From the flow time (t) and distance (a), the velocity is given by $$V = \frac{a}{t}$$

The borehole tracer method is in principle very simple and has been extensively used in groundwater investigations.

This invention is described in detail in the following examples which are provided by way of illustration only and therefore should not be construed to limit the scope of invention.

Example 1

The depiction of solute transport in the vadose zone has been a great center of attraction among the researchers over the few decades. Parameters reveals numerous information through the transportation in the soils. Since the solute transport in the soil is a complex phenomenon which requires appropriate data to meet the requirements. So, experiments were carried out in fabricated columns packed with different type of soils (Table 1). Injection and extraction of tracers in the actual in-situ condition is a very complex task so, in order to minimize the complexity fabricated columns were prepared to meet the requirement. In the previous work dimensions of soil column were mentioned which varies from 10 cm to over 3 m in height and few centimeters to 100 cm in diameter. Keeping in mind, column was prepared with varying texture of soils to test the new CD (Table 1). The soil column was saturated several times with deionized water for one whole day before the day of the respective experiments. In each column, a sample was collected before the start of the experiment for knowing the background value. Tracers were introduced at the top of the sand column. After 3 h of tracer introduction, deionized water was added from the top continuously with constant head of 10 cm and leachates comes out from the bottom are collected.

Figure 10:
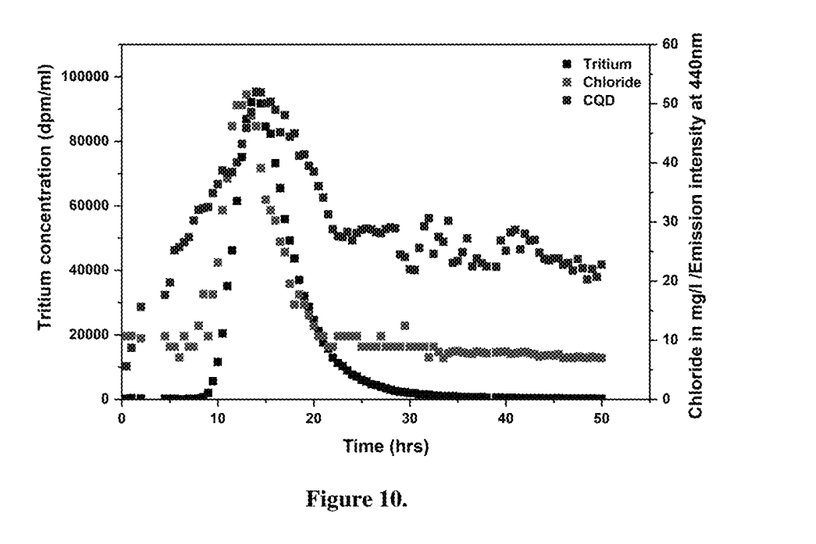
FIG. 10. represents breakthrough curve of three combined tracers (CDs, tritium, chloride) in laboratory simulated soil column. The data indicates the non-sticking nature of the CDs along with the comparative movement of the nanotracer with respect to standards.

Water samples were collected at regular interval of time from the time of leachate arrival for tracer concentration. For coarse and fine sands, the leachate arrived after 1 minute and 30 min respectively. For coarse and medium textured red soil, the leachate arrived within 5 and 10 min respectively. Fluorescent measurements were done in fluorescence spectrophotometer with Excitation intensity: 340 nm and Emission intensity measured in the range: 360-550 nm. The maximum peak emission intensity was observed at 440 nm. Results of comparative movement of 3 tracers namely tritium, chloride and CD in laboratory column A (fine sand) experiment is shown in (FIG. 10).

Figure 13:
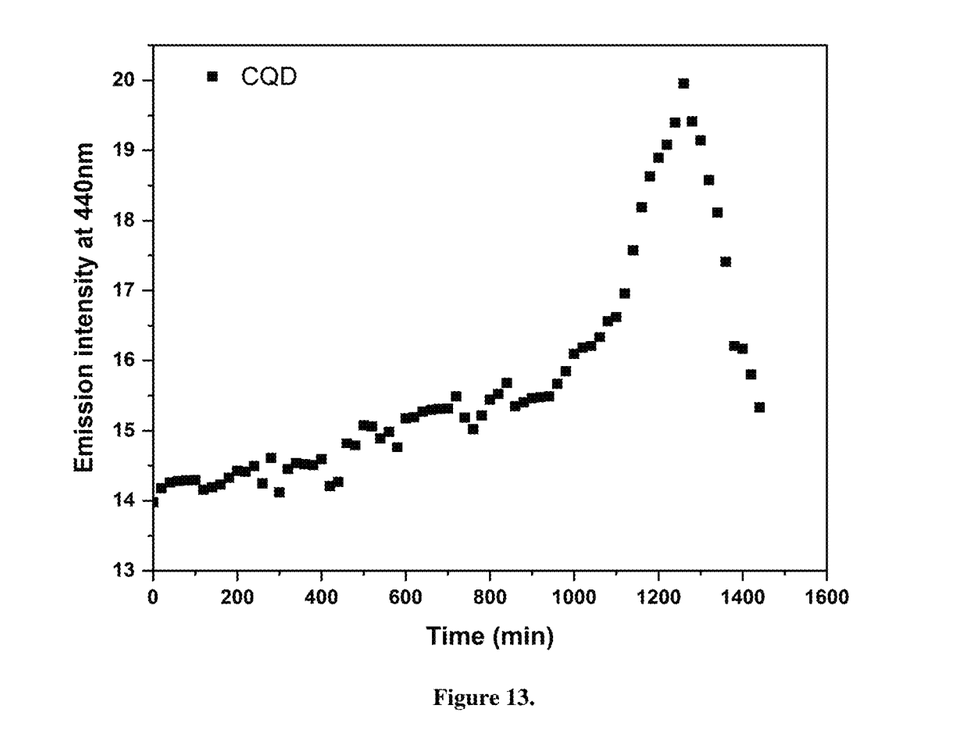
FIG. 13. represents PS S-CD concentration of the observation well. The data indicates that the CDs were traceable in field conditions & in actual well and that it was retrieved between two bore-wells drilled at a gap of 18 m.

The breakthrough curves (FIG. 10) in the laboratory column A study indicate similar pattern for all the three tracers with clear indication of arrival, peak signal and steady decrease in concentration (Gaussian type of distribution). Few high intensity peaks are noticed for CD tracer. Arrival time of tritium and carbon is same (i.e. after 14 h of introduction), while it is only 12.5 h for chloride. Results of comparative movement of two tracers, tritium and CD in laboratory column B (coarse sand) are shown in FIG. 13.

Figure 8:
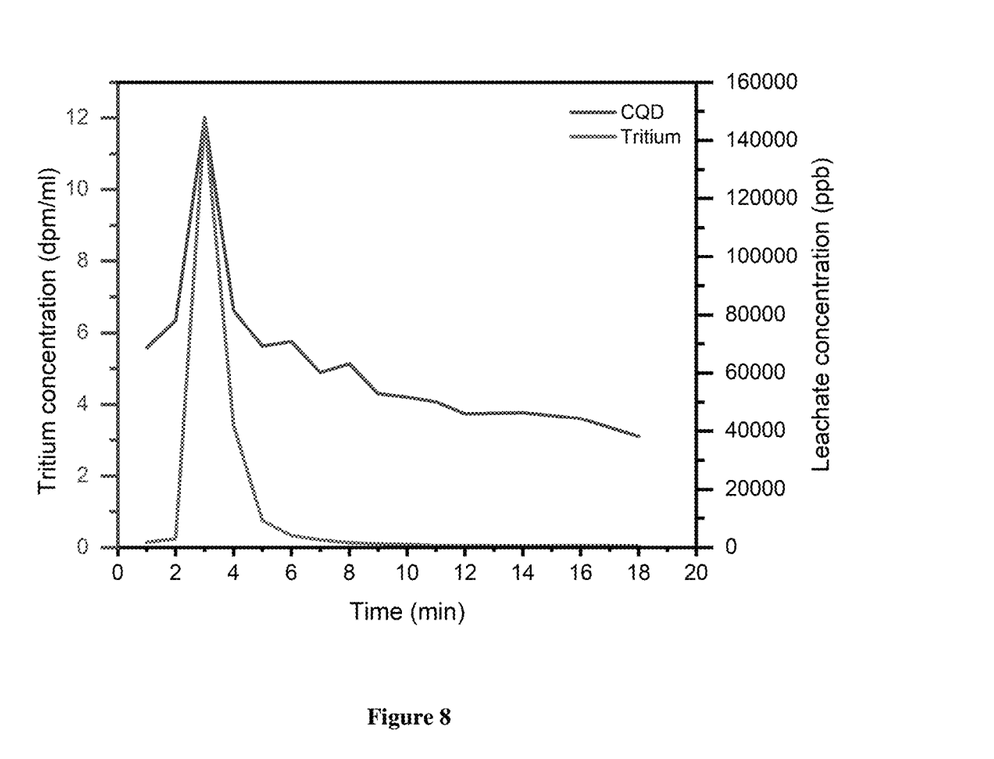
FIG. 8. represents breakthrough curve of two combined tracers (CP+Tritium) for column B.
Figure 9:
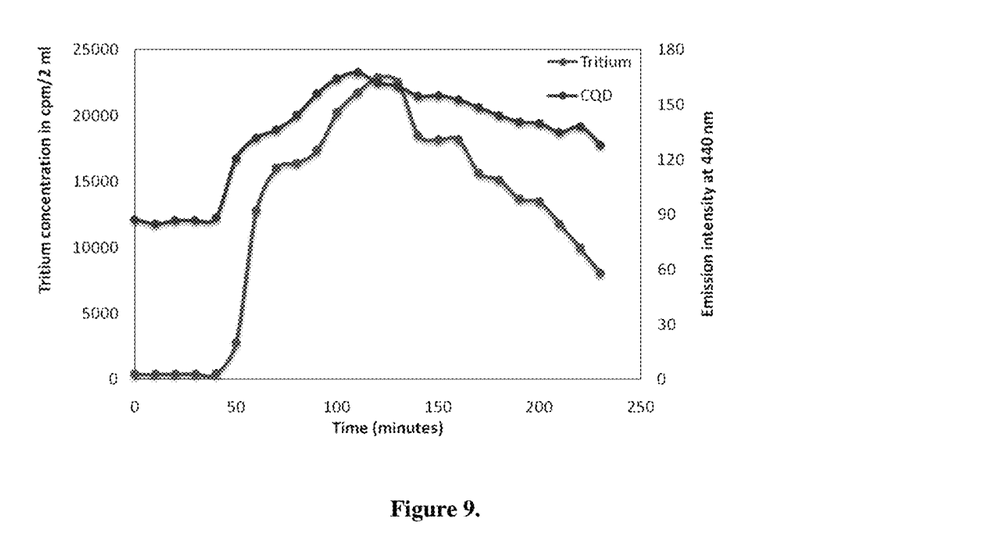
FIG. 9. represents breakthrough curves of comparative tracers' movement for medium textured red soil.

The breakthrough curves (FIG. 8) in the laboratory column B study indicate similar nature has been observed for CD and conventional Tritium tracer in terms of arrival time (~3 min), peak signal etc. The arrival time for both the tracers is much faster in column B than in column A Such observation may be related to the nature of the sand particle present in the column. Slight variation i.e., arrival of peaks at different time interval for CD might be due to stickiness or diffusion of smaller particle into sand. The stickiness observed in the flow pattern for CD sample provides more information to hydrogeologists about the nature of soil/sand sample present in the column as well as the porosity of the column. But from the tritium tracer, not much information can be extracted.

The breakthrough curves in the laboratory columns indicate similar pattern for both the tracers is observed with clear indication of arrival, peak signal and steady decrease in concentration (Gaussian type of distribution) for both the experiment. No other peaks are noticed for CD tracer in both the trial experiments. In the case of medium textured soil, arrival times of tritium and CD nano tracers are same (i.e., at $50^{th}$ min of tracer introduction). Peak activity observed for CD nano tracer is slightly earlier as compared to tritium. The peak tritium activity observed is at $120^{th}$ min, while for nano tracer it is $110^{th}$ min. Thus, all the 4 experiment is successful in terms of behavior of tracer through soil columns. The PSS-CDs showed very low stickiness in various types of soil and sand samples.

TABLE 1

Characteristics of fabricated columns for lab experiments

| Column Medium | Tracer introduced | Duration of the experiment |
|---|---|---|
| (Column A) fine sand 50-100 micron | 100 ml of 0.1 g of carbon sample = 1000 ppm + 10 mL of tritium-25 µCi/mL = 125 microcurie | 3000/50 h |
| (Column B) Coarse sand 1000-1200 micron | 100 ml of 0.1 g of carbon sample = 1000 ppm + 100 ml of 2000 ppm chloride + 10 mL of tritium-25 µCi/mL = 125 microcurie | 18 min/0.3 h |
| (Column C) Coarse textured red soil coarse sand: 65% (2000-500 micron), medium sand: 32% (500-250 microns), fine sand: 2.5% (250-60 microns), silt and clay: 0.5% (<60 microns) | 100 mg of CD tracer in 100 ml water = 1000 ppm CD tracer + 2 ml of 25 microcurie/ml tritium = 50 microcurie | 120 min/2 h |
| (Column D) Medium textured red soil coarse sand: 38% (2000-500 micron), medium sand: 56% (500-250 microns), fine sand: 4% (250-60 | 100 mg of CD tracer in 200 ml water = 500 ppm + 5 ml of 25 micro curie/ml tritium = 125 microcurie | 240 min/4 h |

TABLE 1-continued

Characteristics of fabricated columns for lab experiments

| Column Medium | Tracer introduced | Duration of the experiment |
|---|---|---|
| microns), silt and clay: 2% (<60 microns) | | |

Example 2

Figure 12:
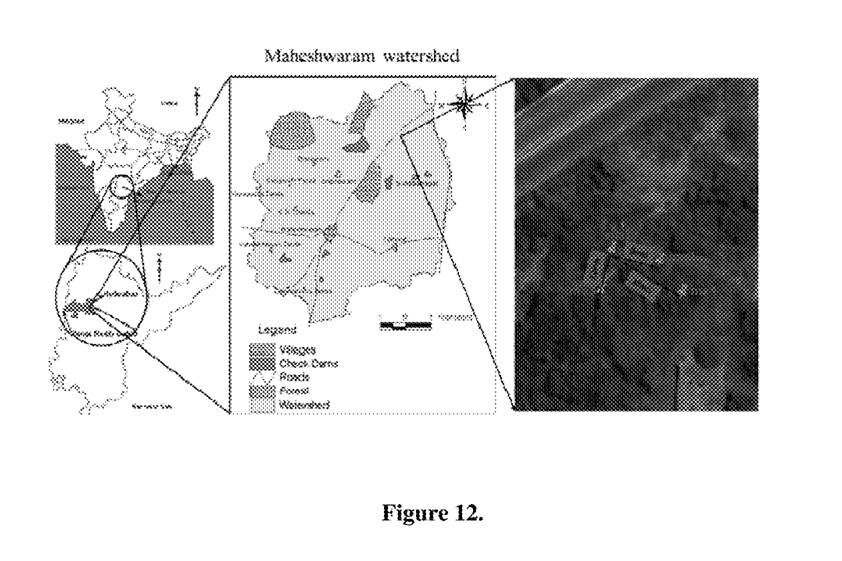
FIG. 12. shows cluster bore wells site at Maheshwaram, Rangareddy district, Telangana.

In order to understand the transport process in fractured formation through CD, tracer test was conducted, which is of vital importance for predicting contaminant migration and waste disposal. To investigate the transport phenomenon through tracer test at varying distance from the injection and acquiring point spatial information in heterogeneous media needs to acquire. Test were conducted which may reveal the subsurface information. At an experimental site in granite terrain, PSS-CD tracer was used for groundwater velocity estimation through multiwall technique under induced condition. The experimental site was selected in such a way that the cluster wells in the study area should connected with micro and major fracture from end to end between injection well and acquiring well, so that the performance of new CD tracer could be justified. The experiment was carried out to test and evaluate CD as water tracer for groundwater flow studies. The site is at a distance of about 30 km from Hyderabad and is located near to Maheshwaram town in Rangareddy district of Telangana State, (FIG. 12). The site area is in granite terrain where multiple bore wells of 6" diameter were drilled up to maximum depth of 50 m to study hydrology of Maheshwaram watershed. Lithological studies shows that the formation up to the depth of 45 m is characterized by weathered and fracture formations. The bore hole test was conducted under induced condition where in, the observation well was pumped continuously using 1 HP submersible pump for creating hydraulic gradient for inducing groundwater flow and also for sample collection of the aquifer water. The details are as follows;

Tracer was injected in BW3 for both the experimental investigations within short span of 2 minutes and thoroughly mixed with the existing well water for 30 min. Submersible pump of 1 HP capacity was installed in BW 2 at 40 m depth and run through 2 KVA generator, which act as sampling well for the experiment 1 and existing 5 HP submersible pump fitted in BW 1 at 45 m depth was used for experiment 2 (Table 3). Water samples were collected at regular interval of time from the beginning of pumping to the end of pumping for both the experiments.

TABLE 2 represents locations of cluster wells in the study area.

| Well no | Lat, Long | Depth (mts) | SWL (mbmp) | Distance from well 1 (mts) |
|---|---|---|---|---|
| 1 | 17.17089, 78.4619 | 60.0 | 12.30 | 0.0 |
| 2 | 17.17088, 78.46201 | 43.8 | 12.31 | 9.0 |
| 3 | 17.17080, 78.46189 | 48.5 | 12.06 | 12.0 |
| 4 | 17.17082, 78.46207 | 23.2 | 14.42 | 18.0 |

TABLE 3

Characteristics of field site convergent tracer experiments.

| Date of test | Tracer used | Injection well | Water column in inj well | CD conc in inj well | Observation/ pumping well | Inj well-obs well distance (m) |
|---|---|---|---|---|---|---|
| 2.5.18 (exp 1) | CD (25 gms) in 5 lts water | BW3 (6" dia) | 36.44 (665 lts) | 37.3 ppm | BW2 1 HP sub pump Run through 2 KVA generator | 18 m |
| 17.5.18 (exp 2) | CD (50 gms) in 10 lts water | BW3 (6" dia) | 36.44 (665 lts) | 74.1 ppm | BW1 5 HP sub pump. Run through AC power supply | 12 m |

Figure 14:
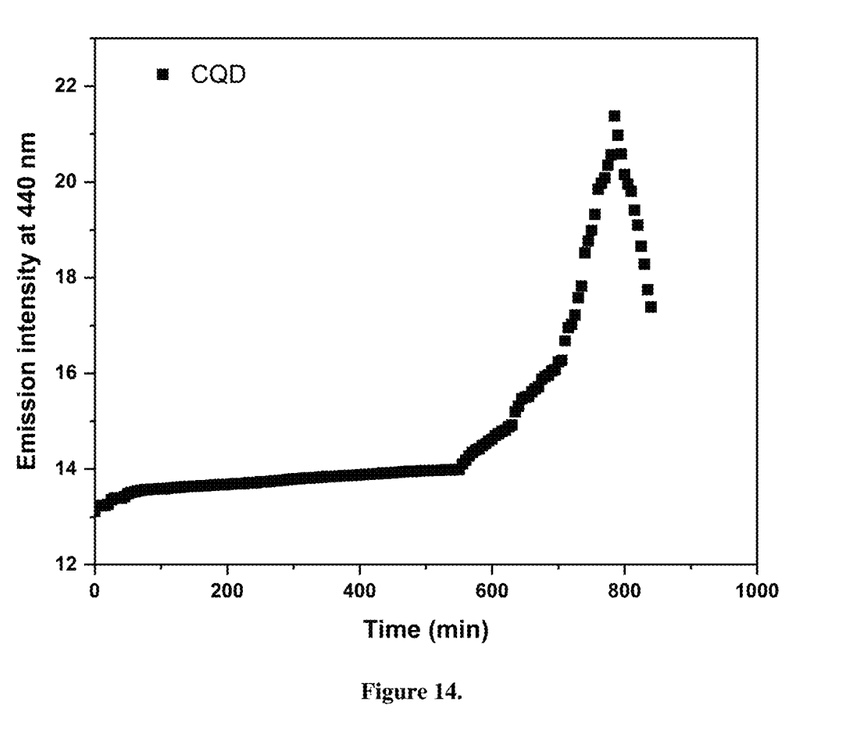
FIG. 14. represents PSS-CD concentration of the observation well. Experiment carried out with different capacity of pump (5 hp) and the lateral distance between the wells are 12 m.
Figure 15:
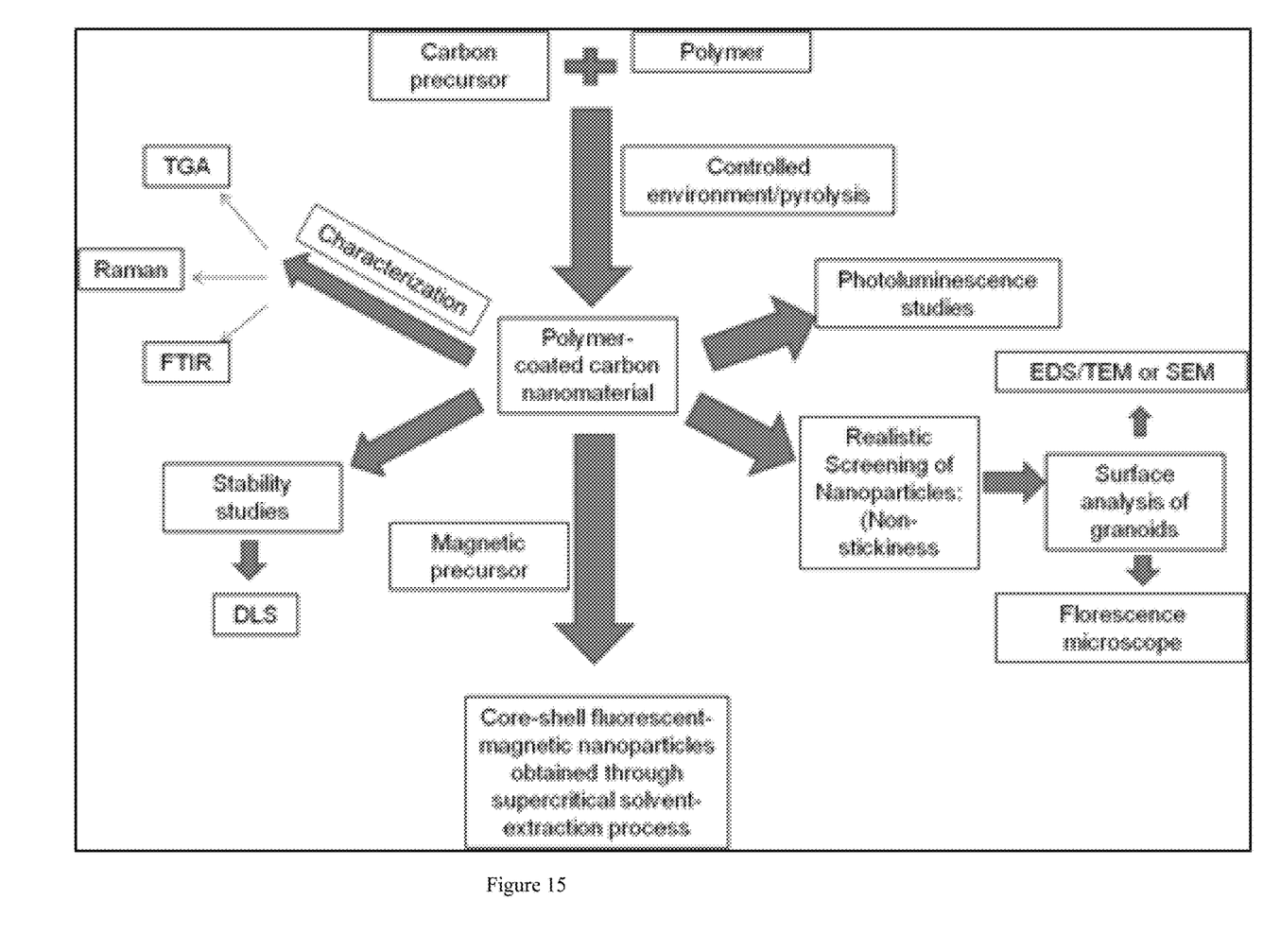
FIG. 15. shows processing of a carbon precursor and a polymer to produce core-shell fluorescent-magnetic nanoparticles obtained through supercritical solvent-extraction.
Figure 16:
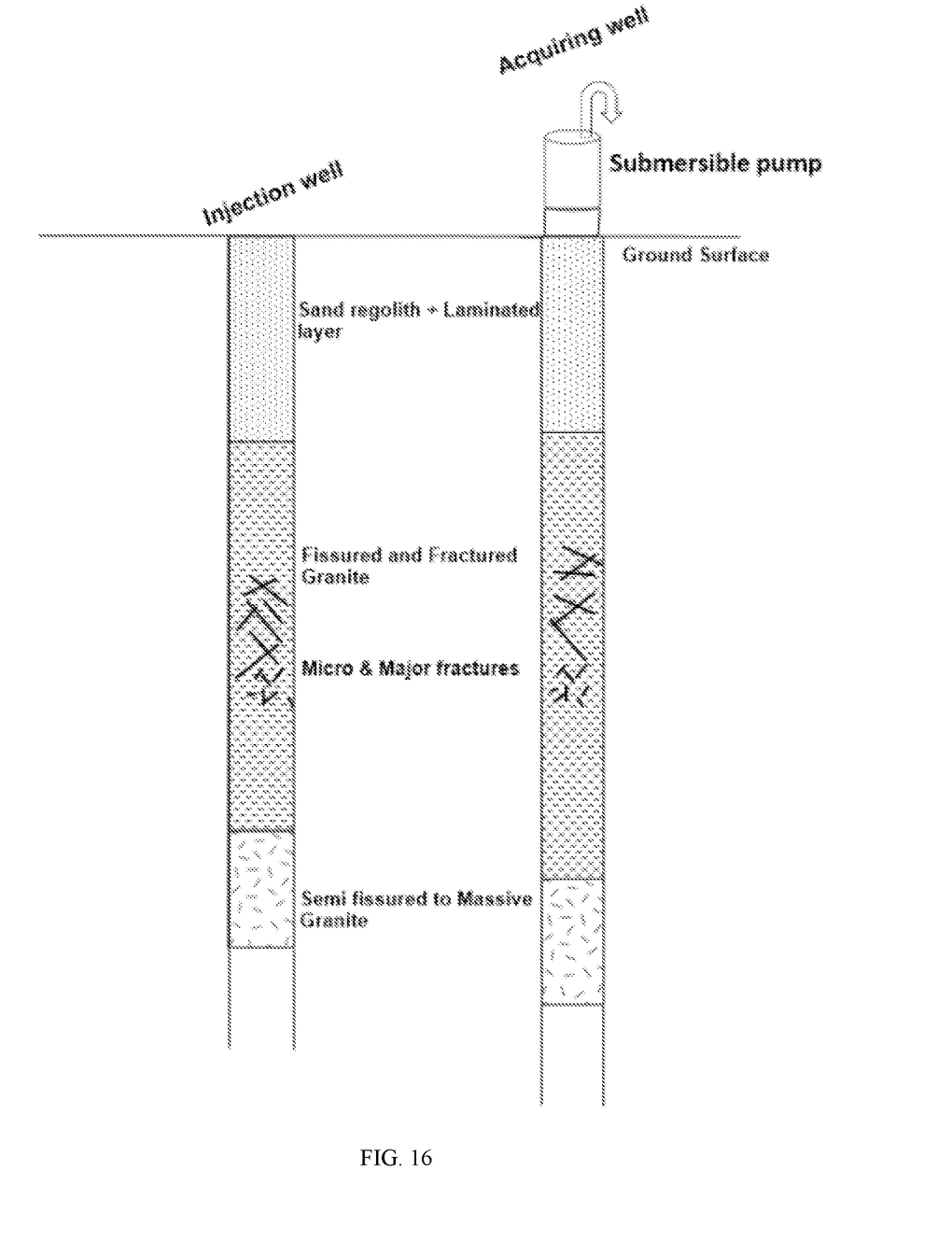
FIG. 16 is a schematic representation for carrying out a method for measuring ground water characteristics.

In the first experiment, CD tracer injected in a BW3 has shown a peak signal of its arrival in observation well BW2 (at a distance of 18 m from injection well) after 1260 min (Table 4 & FIG. 13). The velocity of ground water is calculated as 0.854 m/h or 20.5 m/d. In the second experiment nano tracer injected in a BW3 has shown a peak signal of its arrival in observation well BW1 (at a distance of 12 m from injection well) after 785 min (Table 4 & FIG. 14). The velocity of ground water is calculated as 0.92 m/h or 22.1 m/d. Higher velocity observed in the case of second experiment is due to higher capacity submersible pump fitted in observation well BW1 resulting in higher hydraulic gradient. Thus, the newly developed particle tracer CD could be effectively used as hydrological tracer for evaluating groundwater flow characteristics.

TABLE 4

Results of convergent tracer experiment

| Expt. | Major zone aquifer | | Peak signal arrival after tracer inj (min) | Inj-ob well distance (m) | Hydraulic gradient (%) | Actual velocity (m/d) |
|---|---|---|---|---|---|---|
| 1 | Weathered and fractured | | 1260 | 18 | 13% | 20.5 |
| 2 | -do- | | 785 | 12 | 16% | 22.1 |

Example 3

Cytotoxicity Studies

Figure 11:
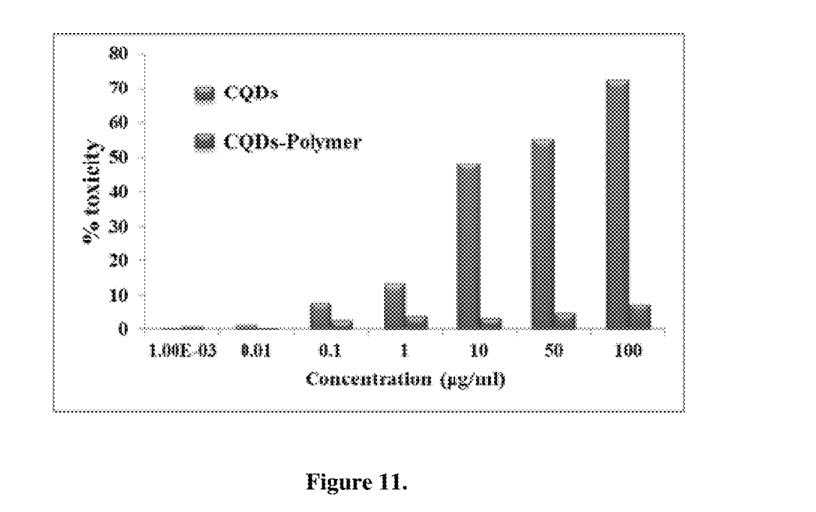
FIG. 11. represents percentage toxicity of CDs (dry powder) and CD-polymer on MDA MB 453 cell line.

The final criteria needed to test the CDs as tracer is the cytotoxicity. It is important that the perfect tracer should have the minimum environmental effect. As synthesized carbon dots (CDs) were tested for cytotoxicity, it shows toxicity to cells with increased concentration. IC50 for CDs is 59.44 (μg/ml) and CDs-polymer is higher than tested value >100 (μg/ml) shown in Table 5. Interestingly CDs prepared with polymer (Jeffamine) sample does not have any toxicity. FIG. 11 shows the percentage cytotoxicity for each and every concentration of CDs and CDs-polymer and it shows that CDs coating with Jeffamine polymer increases its biocompatibility significantly. The reduction in toxicity of CDs with polymer might due to surface modification. This all 'even' shows much less and not any toxicity for cancer cell line. However, percentage viability of cells was above 90% in 100 μM and more than 95% at lower concentrations for both the samples.

TABLE 5 represents minimum toxicity concentration (IC50) for CDs.

| S. No | Formulation | IC50% Con. |
|---|---|---|
| 1 | CDs (dry powder) | 59.44 (μg/ml) |
| 2 | CDs with Polymer (viscous solution) | >100 (μg/ml) |

1. REFERENCES

1. Davis, S N., Thompson, G M., Bentely, G E. and Stiles, S. 1980. Ground-Water Tracers—A Short Review. Groundwater 18 (1), 14-23. https://doi.org/10.1111/j.1745-6584.1980.tb03366.x.
2. Leibundgut, C. 1995. Tracer technologies for hydrological systems. International Association of Hydrological Sciences
3. Maurice, L., Barker, J A., Atkinson, T C., Williams, A T. and Smart, P L. 2011. A Tracer Methodology for Identifying Ambient Flows in Boreholes. Groundwater 49 (2), 227-238. https://doi.org/10.1111/j.1745-6584.2010.00708.x.
4. Sankaran, s., Rangarajan, R. and Dhar, R L. 2005. Delineation of hydraulic connectivity across a dolerite dyke through hydrogeological, geophysical and tracer studies—A case study. Environmental Geology 48(4): 411-419.
5. Puri, S., Kumar, P., Rana, S., Kr, B., Debnath, S., Ghanshyam, C. and Kapur, P. 2014. GIS-Based Geospatial Mapping of Arsenic Polluted Underground Water in Purbasthali Block in Bardhaman, West Bengal. International Conference on Communication and Computing (ICC-2014), At Bangalore.
6. Ramakrishnaiah, C R. and Manasa, N. 2016. Distribution and Migration of Heavy Metals in Peenya Industrial Area, Bangalore, Karnataka, India—A Case Study. Journal of Geography, Environment and Earth Science International 6, 1-13. DOI:10.9734/JGEESI/2016/26361.
7. Drost, W., Klotz, D., Koch, A., Moser, H., Neumaier, F. and Rauert, W. 1968. Point dilution methods investigating ground water flow by means radioisotopes. Water resources research 4 (1), 125-146.
8. Leibundgut, Chris. 1995. Tracer technologies for hydrological systems. Proceedings of an international symposium, Colorado.
9. McCance, W., Jones, O A H., Edwards, M., Surapaneni, A., Chadalavada, S. and Currell, M. 2018. Contaminants of Emerging Concern as novel groundwater tracers for delineating wastewater impacts in urban and peri-urban areas. Water research 146. 118-133.
10. Winter, F. 2006. Using tracer techniques to investigate groundwater recharge in the Mount Carmel aquifer Israel, Ph.D Thesis. Albert ludwing university, Freiburg.
11. Sanford, W E., Hertig, W A. and Herczeg, L. 2011. Preface: Insights from environmental tracers in groundwater systems. Hydrogeology Journal 19, 1-3.
12. Subramanian, S K., Li, Y. and Cathles, L M. 2013. Assessing preferential flow by simultaneously injecting nanoparticles and chemical tracers. Water resources research 49, 29-42.
13. Yuce, G. and Gasparon, M. 2013. Preliminary risk assessment of radon in groundwater: a case study from Eskisehir, Turkey. Isotopes in environmental and health studies 49 (2), 163-179.
14. Salim, H S. 2011. Applications of nanoparticle image velocimetry in nanofluids, Master's Thesis, University of Tennessee.
15. Tcherniak, A., Prakash, A., Mayo, J T., Colvin, V L. and Link, S. 2009. Fluorescence correlation spectroscopy of magnetite nanocrystal diffusion. J. Phys. Chem. C. 113, 844-848.
16. Berkowitz, B. 2002. Characterizing flow and transport in fractured geological media:A review. Advances in Water Resources 25, 861-884.
17. Bodin, J. and Ghislain, F. 2003. Solute transport in a single fracture with negligible matrix permeability: 1. Fundamental mechanisms. Hydrogeology Journal 11 (4), 418-433.
18. James, C. A., Miller-Schulze, J. P., Ultican, S., Gipe, A. D. and Baker, J. E. 2016. Evaluating Contaminants of Emerging Concern as tracers of wastewater from septic systems. Water Research doi: 10.1016/j.watres.2016.05.046.
19. Cohen, M. and Weisbrod, N. 2017. Transport of iron nanoparticles through natural discrete fractures, Water Research. doi: 10.1016/j.watres.2017.11.019.
20. Hung, Y L., Hsiung, T M., Chen, Y Y., Huang, Y F. and Huang, C C. 2010. Colorimetric detection of heavy metal ions using label-free gold nanoparticles and alkanethiols. J. Phys. Chem. C. 114, 16329-16334.
21. Kanel, S R., Goswami, R R., Clement, T P., Barnett, M O. and Zhao, D. 2008. Characteristics of surface stabilized zero-valent iron nanoparticles in porous media. Environ. Sci. Technol. 42, 896-900.
22. Kanj, M Y. Harunar, M., Dhubri, R. and Giannelis, E. 2012. Carbon-based fluorescent tracers as oil reservoir nano-agents, United States Patent Application Publication.
23. Sharma, P., Brown, S., Walter, G., Santra, S. and Moudgil, B. 2006. Nanoparticles for bioimaging. Advances in colloid and interface science 123, 471-485.
24. Divine, C. and Mcdonnell, J. 2005. The future of applied tracers in hydrogeology. Hydrogeology Journal 13. 255-258. DOI:10.1007/s10040-004-0416-3.
25. Geuther, J., Podowski, M., Danon, Y. and Block, R. 2019. Development of a Nanotracer Method to Characterize Nanoparticle Coatings. Isotopes and Radiation: General, 784.
26. Bhattacharjee, L., Manoharan R., Mohanta, K. and Bhattacharjee, R R. 2015. Conducting carbon quantum dots—a nascent nanomaterial. J. Mater. Chem. A 3, 1580-1586. DOI: 10.1039/C4TA05491A.
27. Bhattacharjee, L., Mohanta, K., Pal, K., Koner, A L. and Bhattacharjee, R R. 2016. Polarization induced dynamic photoluminescence in carbon quantum dot-based ionic fluid. J. Mater. Chem. A 4, 2246-2251.

28. Bhattacharjee, L., Pal, Jat, S K., Koner, A L., Ravichandran, J. and Bhattacharjee, R R. 2017. Tuning optical properties of printable carbon quantum dots using near-field environment. Carbon 125, 409-418. https://doi.org/10.1016/j.carbon.2017.09.030.

The invention claimed is:

1. A method for measuring ground water characteristics, the method comprising:
   a. injecting a carbon dot tracer in an injection bore well, wherein the carbon dot tracer comprises polystyrene sulphonate-coated carbon dots having a particle size in a range of 7-8 nm;
   b. mixing the carbon dot tracer and ground water in the injection bore well;
   c. pumping the ground water mixed with the carbon dot tracer from the injection bore well to an acquiring bore well connected with the injection bore well with a micro fracture and a major fracture;
   d. collecting the water samples mixed with the carbon dot tracer at the acquiring bore well; and
   e. measuring fluorescence of the collected water samples to obtain the characteristics of the ground water.

2. The method according to claim 1, wherein the injection bore well and the acquiring bore well are made of hard rock of terrane, wherein the terrane is selected from granitoid rock or basalt.

3. The method according to claim 1, wherein the injection bore well and the acquiring bore well are at a depth of 48 m and 49 m, respectively.

4. The method according to claim 1, wherein the pumping of ground water mixed with the carbon dot tracer is carried out by a submersible pump of 1-5 HP with the in-situ pH in a range of 6-8.

5. The method according to claim 1, wherein the concentration of the carbon dot tracer is 100 ppm in the injection bore well.

6. A method for measuring ground water characteristics, the method comprising:
   a. injecting a polystyrene sulphonate-coated carbon dot tracer in an injection bore well;
   b. mixing the polystyrene sulphonate-coated carbon dot tracer and ground water;
   c. pumping the ground water mixed with the polystyrene sulphonate-coated carbon dot tracer from the injection bore well to an acquiring bore well by a submersible pump;
   d. collecting the water samples mixed with the polystyrene sulphonate-coated carbon dot tracer at the acquiring bore well; and
   e. measuring fluorescence of the collected water samples to obtain the characteristics of the ground water,
   wherein the acquiring bore well is connected to the injection bore well with a micro fracture and a major fracture.

7. The method according to claim 6, wherein the injection bore well and the acquiring bore well are made of hard rock of terrane, wherein the terrane is selected from granitoid rock or basalt.

8. The method according to claim 6, wherein the injection bore well and the acquiring bore well are at a depth of 48 m and 49 m, respectively.

9. The method according to claim 6, wherein the submersible pump is selected from 1-5 HP submersible pumps.

10. The method according to claim 6, wherein the carbon dot tracer is polystyrene sulphonate-coated carbon dots, wherein the polystyrene sulphonate-coated carbon dots have a particle size in a range of 7-8 nm.

11. The method according to claim 6, wherein the concentration of the carbon dot tracer is 100 ppm in the injection bore well.

* * * * *